(12) United States Patent
Schaevitz et al.

(10) Patent No.: US 11,109,801 B2
(45) Date of Patent: Sep. 7, 2021

(54) METHOD OF MEASURING EFFICACY OF TREATMENT FOR AN AUTOIMMUNE DISEASE IN VIVARIUM ANIMALS

(71) Applicant: Recursion Pharmaceuticals, Inc., Salt Lake City, UT (US)

(72) Inventors: Laura Schaevitz, Los Gatos, CA (US); Daniel J. Ford, Belmont, CA (US)

(73) Assignee: Recursion Pharmaceuticals, Inc., Salt Lake City, UT (US)

( * ) Notice: Subject to any disclaimer, the term of this patent is extended or adjusted under 35 U.S.C. 154(b) by 238 days.

(21) Appl. No.: 16/578,298

(22) Filed: Sep. 21, 2019

(65) Prior Publication Data

US 2020/0015741 A1 Jan. 16, 2020

Related U.S. Application Data

(63) Continuation of application No. 15/282,364, filed on Sep. 30, 2016, now Pat. No. 10,420,503.

(51) Int. Cl.
*A61B 5/00* (2006.01)
*A61B 5/11* (2006.01)
(Continued)

(52) U.S. Cl.
CPC ............ *A61B 5/4848* (2013.01); *A01K 1/031* (2013.01); *A01K 29/005* (2013.01); *A61B 5/1118* (2013.01); *A61B 5/4076* (2013.01); *A61B 5/4842* (2013.01); *A61B 5/7282* (2013.01); *A61B 5/7257* (2013.01); *A61B 2503/40* (2013.01); *A61B 2503/42* (2013.01); *A61D 99/00* (2013.01)

(58) Field of Classification Search
CPC ... A61B 5/4848; A61B 5/4842; A61B 5/4076; A61B 5/1118; A61B 5/7282; A61B 5/7257; A61B 2503/40; A61B 2503/42; A01K 1/031; A01K 29/005; A61D 99/00
See application file for complete search history.

(56) References Cited

U.S. PATENT DOCUMENTS

2011/0104717 A1* 5/2011 Fantl ................... A61K 31/704
435/7.21
2018/0092591 A1* 4/2018 Ford ................... A61B 5/4076
(Continued)

*Primary Examiner* — Sean P Dougherty
(74) *Attorney, Agent, or Firm* — Kim Rubin Patent Agent

(57) ABSTRACT

A method of measuring efficacy of test treatment of an autoimmune disease in an animal in a vivarium is described. Animal activity data is collected at multiple times during the night. Sequential time regions of the night are identified as high-activity, activity-drop, or low-activity regions. Embodiments are described to quantify a drop, during the night, of an animal's activity level. These quantified activity-drop scalars for consecutive nights are accumulated in an animal health dataset. This dataset is compared to healthy animals, a standard of care or a reference treatment for the first disease to determine efficacy of the test treatment. One embodiment quantifies an activity-drop by fitting straight-line curves through the data in the three nightly regions. Other embodiment uses a Fourier transform on a circle, LASSO, RANSAC or regression analyses for curve fitting. Another embodiment compares areas under data curves in the regions. Animals may be housed in cages with other animals.

3 Claims, 12 Drawing Sheets

(51) Int. Cl.
 *A01K 1/03* (2006.01)
 *A01K 29/00* (2006.01)
 *A61D 99/00* (2006.01)

(56) References Cited

U.S. PATENT DOCUMENTS

2018/0092596 A1* 4/2018 Ford .................... A61B 5/7282
2018/0092597 A1* 4/2018 Schaevitz ............ A61B 5/4076
2018/0092605 A1* 4/2018 Schaevitz .............. G16H 50/20

* cited by examiner

ONE 12-HOUR NIGHT PERIOD

METHOD OF MEASURING EFFICACY OF TREATMENT FOR AN AUTOIMMUNE DISEASE IN VIVARIUM ANIMALS

Related patents include U.S. Pat. No. 10,188,321 issued Jan. 29, 2019, by the same inventors; U.S. Pat. No. 10,420,503, by the same inventors; and U.S. Pat. No. 10,244,979 issued Apr. 2, 2019.

BACKGROUND OF THE INVENTION

Prior art methods of animal studies involving diagnosis and treatment of multiple sclerosis (MS) involve manual observation of rodents in a vivarium, and then making subjective ratings of up to 16 observed behaviors. These subjective ratings are aggregated into a disease activity index (DAI). Other MS health indexes are known as a multiple sclerosis functional composite (MSFC) index or a functional system score (FCC). Observations are typically done daily, with ambient illumination suitable for human observation, rather than the darkness, the normal nocturnal activity period of the animals.

Weaknesses of this prior art include inconsistent, subjective ratings both within a study and between studies; high expense due to high human labor; limited study size due to expense; poor measure of animal activity due to observations during a unnatural (nocturnal) activity period when animal activity is low for both healthy and sick animals; limited measurement or recording of other animal health metrics, such as eating. Eating binges are unlikely to be detected. In particular, human observations are inherently qualitative rather than quantitative.

SUMMARY OF THE INVENTION

Embodiments of this invention overcome the above-cited weaknesses of prior art.

Continual electronic, automated observation of animal behaviors during the animal's natural nocturnal activity period permits far more consistent, compressive, quantitative and capable data collection and analysis than prior art. Electronic hardware and software are necessary for practical embodiments of this invention, including cages free of electrical penetration, infrared (IR) lighting and cameras, and extensive data communication, storage and computational capability. Real-time animal ID is necessary to observe behaviors of specific animals in cages with other animals (multi-housed).

In order to understand embodiments, it is necessary to first establish terminology related to the timeline and actions involving animals in a vivarium study. Such terminology below is intended to be consistent with its meaning in the art; however, in some cases it is necessary to restrict or clarify meaning as used for embodiments. Construction of terms should defer to the definitions herein when they differ from common usage in the art; otherwise, the terms have the definitions in the art. The applicable art is: animal studies in vivaria of multiple sclerosis (MS).

We divide the time period of a study into twelve consecutive time periods or events, as follows:

1) Prestudy—a time period or information prior to the start of the study. Such information may include a birthdate, animal breed, genotype, weight, and history up Acclimation. Such information may be extensive.

2) Acclimation—a time period prior to traditional start of study periods, ending at Baseline. However, such Acclimation may be important so that Baseline data is consistent. Acclimation is normally in the home cage living in home cage conditions that are the same or compatible with home cage conditions during the study.

3) Baseline—a time period at the start of a study when behavior of the animal is recorded prior to any treatment, or change to the animal, or change to its environment. Baseline data collection typically includes activity measurement and weight; however, actions related to vivarium operation, requirements of a study and data collection during Baseline may vary widely. Many metrics for the animal will be measured as a percent of Baseline, such as activity or weight. Embodiments include, and claims should be construed to include metrics, methods, and values as a percent of an animal or cohort's Baseline.

4) Induction—a point in time when some action is performed on the animal, such as an injection. Induction details may vary considerable. For MS, induction might be a disease that causes or simulates MS.

5) Health Drop—Following Induction immediately, or after a short time, for induced MS, the health of the animal falls off rapidly. This period is sometimes called an, "acute response." The Health Drop period is from Induction, or shortly thereafter, until start of Prodromal period. Note that Health Drop is a time period, typically longer than one day. "Activity drop" is a different term used herein to refer to a change in activity for one animal during a night. Such an activity-drop is typically a few hours.

6) Prodromal—A period of time following the rapid Health Drop, up until the start of the Onset Drop time period. In some studies, such for prophylactic treatment, treatment may begin in the Prodromal period.

7) Onset Drop—A period of time following Prodromal where health again drops rapidly, until Onset. In some studies, such for prophylactic treatment, treatment may be begin in the Onset Drop period 8) Onset—Onset is either a point in time or a brief time period around when the animal is the sickest. The Onset time is "assigned" to an animal or possibly to a cohort. Typically, conditions for Onset are specific criteria or factors related to a study. For example, following Induction, an animal's health may clearly and significantly drop, but perhaps not sufficiently to decide that an animal has a disease or is sick enough for Enrollment. In such cases, there may be no formal Onset assigned to that animal. Also, an animal may get sicker following the assigned or quantitatively determined Onset point. Onset is often the point in time for a treatment, or for the start of a treatment, although Onset is not always aligned with treatment. It is important to note that a treatment may start prior to Onset, such during a Prodromal period. Such a treatment may be viewed as "prophylactic," although this term may not be completely accurate, since in a Prodromal period the animal is by definition less healthy than its Baseline; or the because the treatment may not prevent Onset. Onset may be determined by a metric that is not identical to, or claimed to be, "health." For example, Onset may be determined by animal motion or other activity, yet a health metric may include additional or other inputs. Claimed embodiments explicitly include treatments prior to Onset and prophylactic treatments.

9) Enrollment—Enrollment is the process of enrolling the animal in a study. Enrollment, by itself, is neither an action upon the animal nor an exact moment in time, although the decision to enroll an animal almost certainly has an impact on data collection and data analysis, and most likely, treatment, if any. Enrollment of an animal is not mandatory as it often depends on if the animal, or if the data collected, meet some criteria. Enrollment may be retroactive. Enrollment may be 100%. Enrollment is sometimes viewed as a date at the same time as Onset or the same time as treatment, but these associations are somewhat arbitrary.

10) Recovery—A time period following Onset when the animal regains some of its prior health. Health during Recover typically begins with a ramp up, although there may be different shapes to the Recovery health curve.

11) Steady State—A time period of variable length following Recovery where the health of the animal is relatively constant, although it may slowly increase or slowly decrease during Steady State. A study may be terminated during Steady State, or the time period may be terminated for other reasons. The Steady State period is sometimes considered part of Recovery. Thus data collected during "Recovery" may be collected during Steady State as defined here.

12) Relapse—Many animals, if given enough time, will Relapse from Steady State. Studies are often terminated prior to Relapse.

Important comments regarding above time periods or events are discussed below under Detailed Description of the Invention.

From the above term definitions, we may now provide a summary of embodiments.

Following a Baseline period and Induction, an animal's activity is measured automatically multiple times per night. The course of activity during the night follows certain patterns. By analyzing these patterns various predictions may be made and efficacy of treatment measured. Activity may initially be high, followed by a rapid drop, followed by a lower level of activity. Embodiments measure the time and amplitude of the activity-drop during the night. Some embodiments consider the relative activity between the high-activity level and the low-activity level. Some embodiments adjust or compensate a measurement with a minimum activity level during the night or with an animal's activity as measured previously during its Baseline, prior to Induction.

Based on these measurements, computations and physical elements, in one embodiment, MS may be detected early in the study, prior to Onset. In another embodiment, the severity of MS may be predicted, where severity relates to the animal's health during its future Steady State. In another embodiment, the efficacy of treatment may be measured during Steady State or predicted earlier than Steady State. In another embodiment, data using the methods described is collected.

Details of embodiments described below provide quantitative ranges and method details of embodiments, and necessary physical limitations.

In a study with a treatment cohort and a non-treatment cohort, it is important that the animals in each cohort be as otherwise equal as possible so that any differences between the two cohorts may be attributed only to the treatment or non-treatment. Dividing up animals with some known differences, such as weight or Baseline health, evenly into two or more cohorts is a process known as randomization. It is important to know as early as possible any differences that will impact randomization. One such difference may be whether induction will make an animal sick or not. Another such difference may be how sick an animal would get with no treatment. Therefore, predictors made by embodiments of this invention are useful for such purpose.

DETAILED DESCRIPTION

Descriptions and scenarios herein are non-limiting examples.

A study often runs formally from Baseline through some portion of Steady State. However, an Acclimation period may nonetheless be important to establish a proper baseline for animal behavior. Placing animals into a new habitat requires some adaptation by the animal. For example, animals experience jet lag. Because of strong nocturnal behavior of mice, for example, they must adjust to a new time zone for behavior to be consistently measured. A temporary stress level of animals adapting to a new cage and possibly new cage mates needs to abate.

Please refer to the named, twelve different time periods or events within one study above, under Summary Description.

Device and methods of embodiments comprise various combinations of: a vivarium with animal cages free of electronic penetrations; continuous or continual video recording of the cage interior adapted to view all possible locations of animals in the except for burrowing under bedding or in opaque nesting chambers; infrared lighting outside of the range of animal vision; infrared camera; a wireless scale; ability to track the location and identity of different animals in real time in a single cage; video motion analysis; electronic animal identification; electronic connectivity from cage monitoring electronics to aggregated data analysis and recording equipment.

Figure 1:
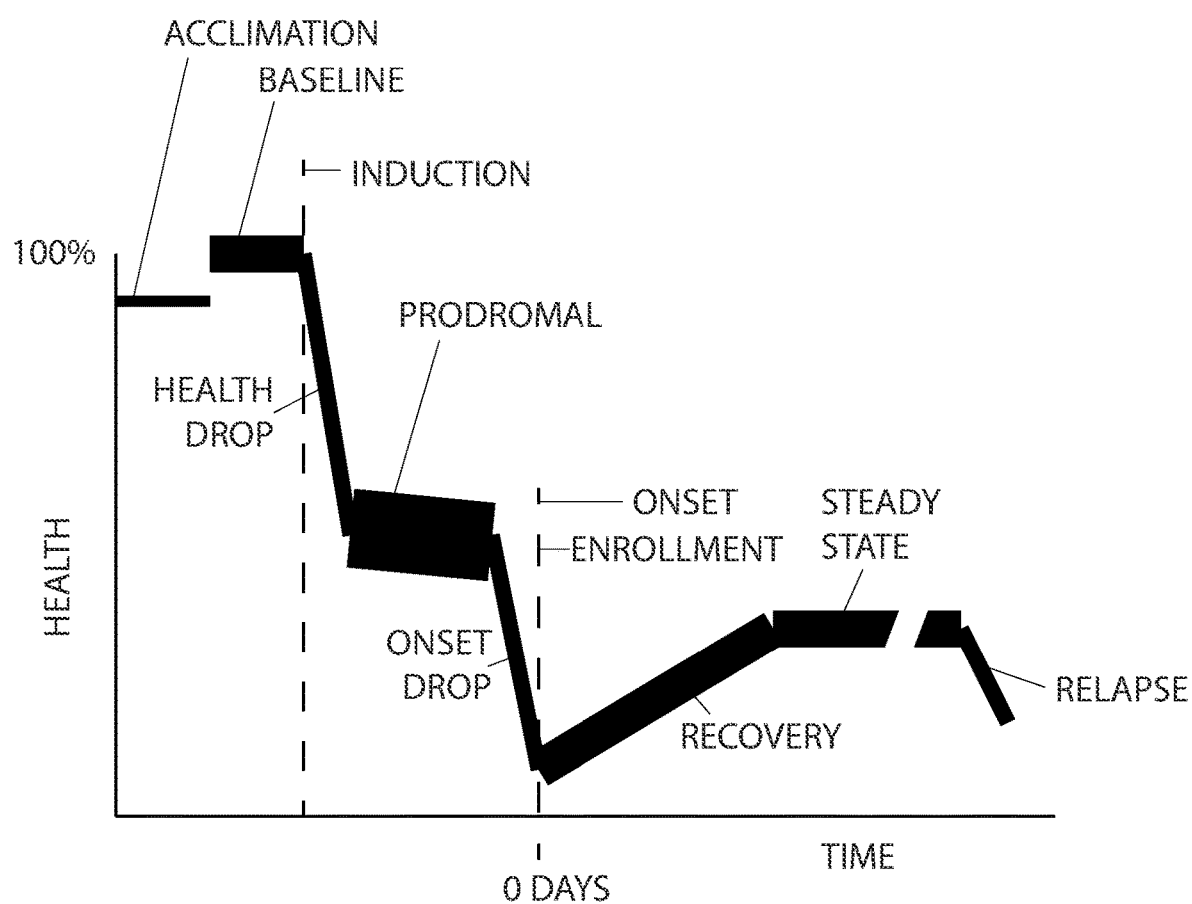
FIG. 1 shows a generic timeline with terminology.

FIG. 1 shows a schematic representation of eleven of the twelve different study time periods or events identified by name above. This exemplary and schematic graph is nominally for one group of animals, a single cohort, of a single study. It may represent data for a single animal, or for more than one cohort. A single study often has more than one cohort, such as treated and untreated animals. A control cohort may be the untreated animals, or a control cohort may not be part of a current study. For example, a control group may comprise known behaviors consistent with the treated animals if untreated, or may be known behaviors consistent with a standard of care for a disease or condition. PRE-STUDY is not shown in the Figure; that would be data to the left of the graph in the Figure. Although PRESTUDY is a time period, the importance of PRESTUDY is primarily the large amount of data about the animals in the cohort, such as type of animal, birthdate, genotype, and source. The horizontal axis in this Figure is time, as is the horizontal axis in FIGS. 2-7. In this Figure, Day 0 is ONSET. The scale of the time axis is roughly days, such as 10 to 60 days. The vertical axis is HEALTH, measured in arbitrary units as will be discussed further below. 100% health in this graph means some Baseline health for the animals in a study. Schematically, the thickness of the line segments, such as the PRODROMAL time period, may generally represent a standard deviation of the measurements for the animals in the cohort. ENROLLMENT is discussed in more detail elsewhere herein.

The ACCLIMATION period is often not considered part of the time for a study. However, the ACCLIMATION time period is important so that the animals in a study have reached a steady state with respect to their current environment in the vivarium, such as the day and night time periods; cage and husbandry attributes such as water, food, bedding, exercise equipment, and temperature; stress level, cage mates and the like. Since data may not be collected during ACCLIMATION, this period is shown in the Figure as having no standard deviation. The length of ACCLIMATION, for mice, may be in the range of one to 10 days or longer. Three days may be an exemplary time length.

The BASELINE period is the time during which animals are observed to establish Baseline behavior. Typically there is no treatment or interference with the animals' normal activity. Baseline activity is often monitored and recorded to establish a baseline value of health for computations, and may be used for randomization. The activity for all animals in the cohort or all animals in the study may be averaged during the Baseline and this activity level, a scalar, used to set 100% health. However, health measurements and other units may be used, including baselines that are consistent across numerous studies. In the art, there are numerous metrics and units for health. Often, sickness is measured in place of health, realizing that the two terms are inverse of each other, and thus may be interchanged by inverting graphs and adjusting for units, baselines, scale, and the like. One such unit of sickness is Disease Activity Index (DAI), often in units of zero to five, in half integer increments. The art describes how to measure a DAI for particular diseases, such as multiple sclerosis (MS). In prior art, a DAI for an animal is a result of brief, manual short-term observations, usually during daytime. Another unit of sickness is called an Experimental Autoimmune Encephalomyelitis, or EAE, score. Units for a health metric, index or units may be an activity measurement. Such an activity measurement may be manual or automated. If automated, units of measurement may be distance traveled in a time window, travel speed (peak or average) during a time window, distance traveled during a time window, or other measures of animal activity. A time window may be one minute to 15 minutes, or shorter or longer. Measured activity may also or alternatively include time, distance, speed or time on an exercise apparatus, such as a running wheel or climbing ladder. Exemplary units might be seconds; seconds/hour; cm; cm/hour, and the like. Despite have real numbers from real observations, graphs and computations are often done using percentages, as indicated in this Figure. Conceptually, there is little difference between units or percentages on the vertical axis. For some studies and embodiments, normalization to a percentage may be appropriate, particularly for measuring changes in health for particular animals or a particular cohort. For other studies and embodiments, consistent physical units or units taken from prior art may be more appropriate, particularly for comparisons of absolute activity between studies. The scope of claims should be construed to include activity measured in physical units, units from the art, and in percentages, normalized or not.

The reader is cautioned that there are two very different meanings of the word, "baseline." As both different meanings are extensive in the art, context is critical for understanding which meaning to apply. The first meaning is the one above that refers to a specific time period, BASELINE, or life of an animal, in a study, to establish the "normal" behavior of the animal prior to action to the animal that might cause it to depart from such normal behavior. Such a period might be five days prior to INDUCTION, for example. The second meaning is some value that is used computationally. This value might be a numeric "floor," for example, which might be subtracted from some measurements so as to create a new number that is "above the floor." This second meaning of baseline might be a reference value to which some other measure is compared, as a second example, normalized so that the result is now expressed as a percentage of the value.

For this second meaning of baseline, there are multiple ways that such a value might be determined or sourced, which varies based on the type of study, the purpose of a measurement and the desired specific outcome of a computation. Such a baseline value may have one of five different sources: (1) from one specific animal; (2) from one specific study or cohort; or from a specific group of studies or group of cohorts; (3) from a value associated with a specific breed, genotype; or another industry provided value; (4) a fixed value; (5) no baseline. In method (5), a baseline number would be zero if its application is to be subtracted, or 100% if its application requires multiplicative normalization. All five such sources are specifically claimed as embodiments for methods that use a baseline value.

INDUCTION is shown in the Figure as a vertical dotted line. INDUCTION is typically a single point in time, rather than a time period. However, it may be useful to consider INDUCTION as a time period, such as one day. The exact nature of INDUCTION depends on the study and may vary widely. It may involve an injection, as one example. Sometimes, at the point of INDUCTION animals in a study will be divided into two or more cohorts, when more than one method of INDUCTION is used. See ONSET below, for a more common time to break a study group into cohorts. If MS is induced, animals can be expected to start getting sick immediately after INDUCTION.

Discussion herein will be for MS unless stated otherwise. Note, however, that many of the methods and embodiments described herein, including claims, apply also to other diseases or to data collection alone. Methods, application of methods, including methods of treatment, to other diseases, including human diseases, and for observations not in a vivarium, may be claimed. Other diseases include autoimmune diseases and encephalomyelitis symptoms and diseases. Other embodiments include health measurements for a wide variety of applications, such as quantifying genotype behavior, determining efficacy or impact of environmental factors, and the like. Devices to implement such methods or applications are also claimed.

HEALTH DROP is a time period following INDUCTION. During this time period, the health of an animal induced with MS drops rapidly.

PRODROMAL is a time period following HEALTH DROP. During this time period, the health of the animal is relatively constant or may drop more slowly than during HEALTH DROP. This slow rate of health decline is shown conceptually by angle of the thick PRODROMAL line segment in the Figure. The relative health of the animal during its PRODROMAL period may vary. This variation is shown conceptually by the thickness of the PRODROMAL line segment. Note that thickness of line segments in this Figure may be viewed as a standard deviation of measurements of a cohort. However, they are not intended to be to scale in this Figure. The health level of the PRODROMAL period may range from 20% to 80% of Baseline (or Baseline minus a minimum health), or may range for 30% to 70%, or may range from 40% to 60%, or another range. The health level of the PRODROMAL period may be measured or discussed relative to Baseline health, or zero health, or a minimum health level, or a computational combination of these.

ONSET DROP is a time period following PRODROMAL. In some ways the PRODROMAL time period may be viewed as a break in the HEALTH DROP of the animals from BASELINE to ONSET. The ONSET DROP period ends nominally at ONSET.

ONSET is a specific time, or limited time window such as one day, that is considered to be the start of the disease, for study purposes. Commonly, ONSET is also when a treatment under test starts. Often, it is at ONSET when a study group is broken into cohorts, such as treated and untreated. ONSET may alternatively be identified as a treatment date or time. It is common in the art to set the time axis to Day zero at ONSET or treatment day. The single graph in this Figure is conceptually for a single cohort. As will be seen in later Figures, often graphs for different cohorts are overlaid. Depending on the purpose or embodiment, multiple cohorts or multiple study graphs may be aligned on the time of INDUCTION, or on the time of ONSET, or aligned by some other method. ONSET may be determining by observing that the animal's health drops below a threshold, or may be an arbitrary day, such as a treatment date for an entire cohort, or may be the minimum health of an animal. It may be a computed date or time, particularly one computed or predicted ahead of ONSET, such as by computations or methods responsive to the HEALTH DROP, PRODROMAL and ONSET drop measurements, or any combination.

RECOVERY is a time period following ONSET when animals get healthier. The shape of the RECOVERY period may be approximately a straight-line as shown, or may be approximately an exponential increase, or may be approximately an inverse exponential curve towards a STEADY STATE asymptote, or some combination of theses, such as an "S" shape. Such variations in shape are relevant for curve fitting applications, methods and steps. A study may end during the RECOVERY time period.

STEADY STATE is a time period following RECOVERY. It is characterized by an approximately stable health of the animal, although it may have a slow increase or decrease. A study may end during the STEADY STATE time period. The length STEADY STATE often varies considerably, RELAPSE may occur at any time, for MS and for other diseases. This unpredictability of the length of STEADY STATE is shown by the break in the line segment in the Figure.

RELAPSE is a common phenomenon, following STEADY STATE, for MS and for other disease. Indeed, MS is often characterized by multiple RELAPSE and recover periods. Studies may or may not include a RELAPSE time period in the study.

The terminology and explanations above and shown schematically in FIG. 1 are relevant to the proper construction and scope of claims and embodiments.

Embodiments are specifically claimed for additional limitations in claims that limit a step or multiple steps to one or more of the above time periods.

Figure 2:
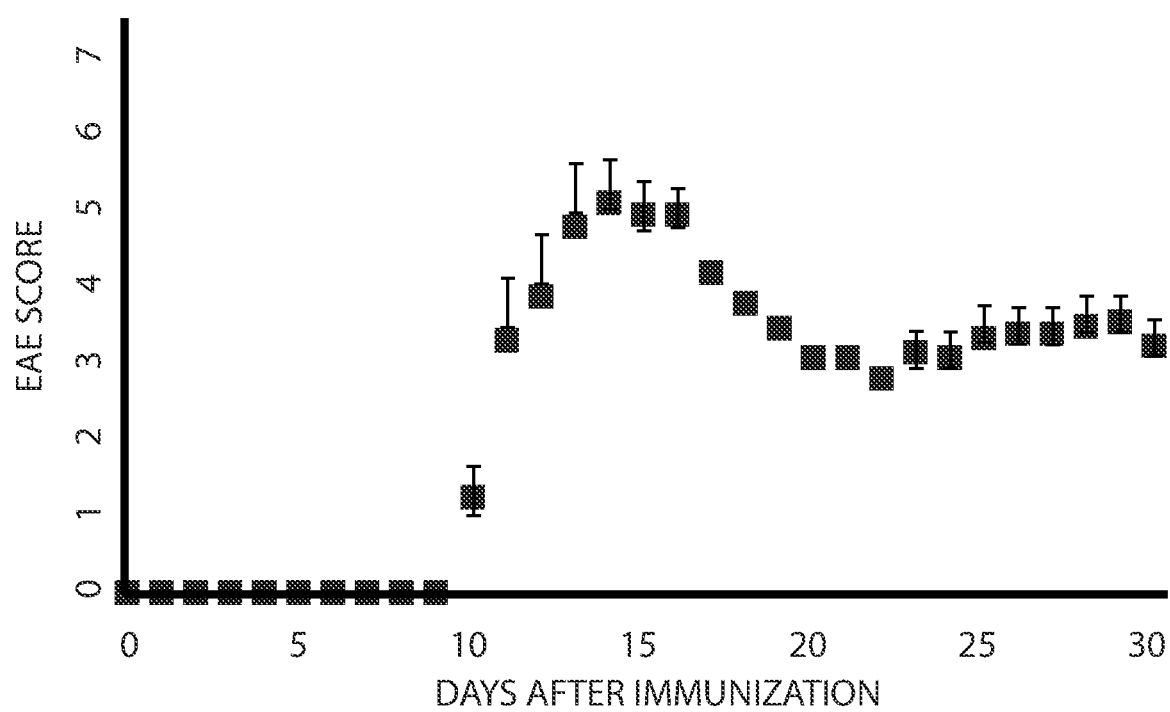
FIG. 2 shows prior art.

FIG. 2 shows exemplary prior art observations for a wide variety of studies. The horizontal axis is time, where zero is set to INDUCTION. The vertical axis is sickness, rather than health such as shown in FIG. 1. Thus, this graph is generally inverted from the exemplary graph in FIG. 1. Here, baseline is shown as a zero EAE SCORE. Note that days 10 through 15 are roughly the time periods of ONSET DROP, PRODROMAL, and ONSET DROP. Note that the PRODROMAL period is not distinct, although though it might be days 12-13. The PRODROMAL time period is not typically recognized in MS prior art studies. Such clear, quantitative recognition of the PRODROMAL time period is an unexpected benefit of embodiments. ONSET is day 15. RECOVERY is days 16-23. STEADY STATE is roughly days 24-30. This prior art graph is taken from FIG. 1 of the publication: Bittner, S., Afzali, A. M., Wiendl, H., Meuth, S. G.; "Myelin Oligodendrocyte Glycoprotein (MOG35-55) Induced Experimental Autoimmune Encephalomyelitis (EAE) in C57BL/6 Mice;" *Jove Journal of Visualized Experiments* (86), e51275, doi:10.3791/51275 (2014); published Apr. 15, 2014. Of key importance in this prior art is that observations are taken once per day.

Figure 3:
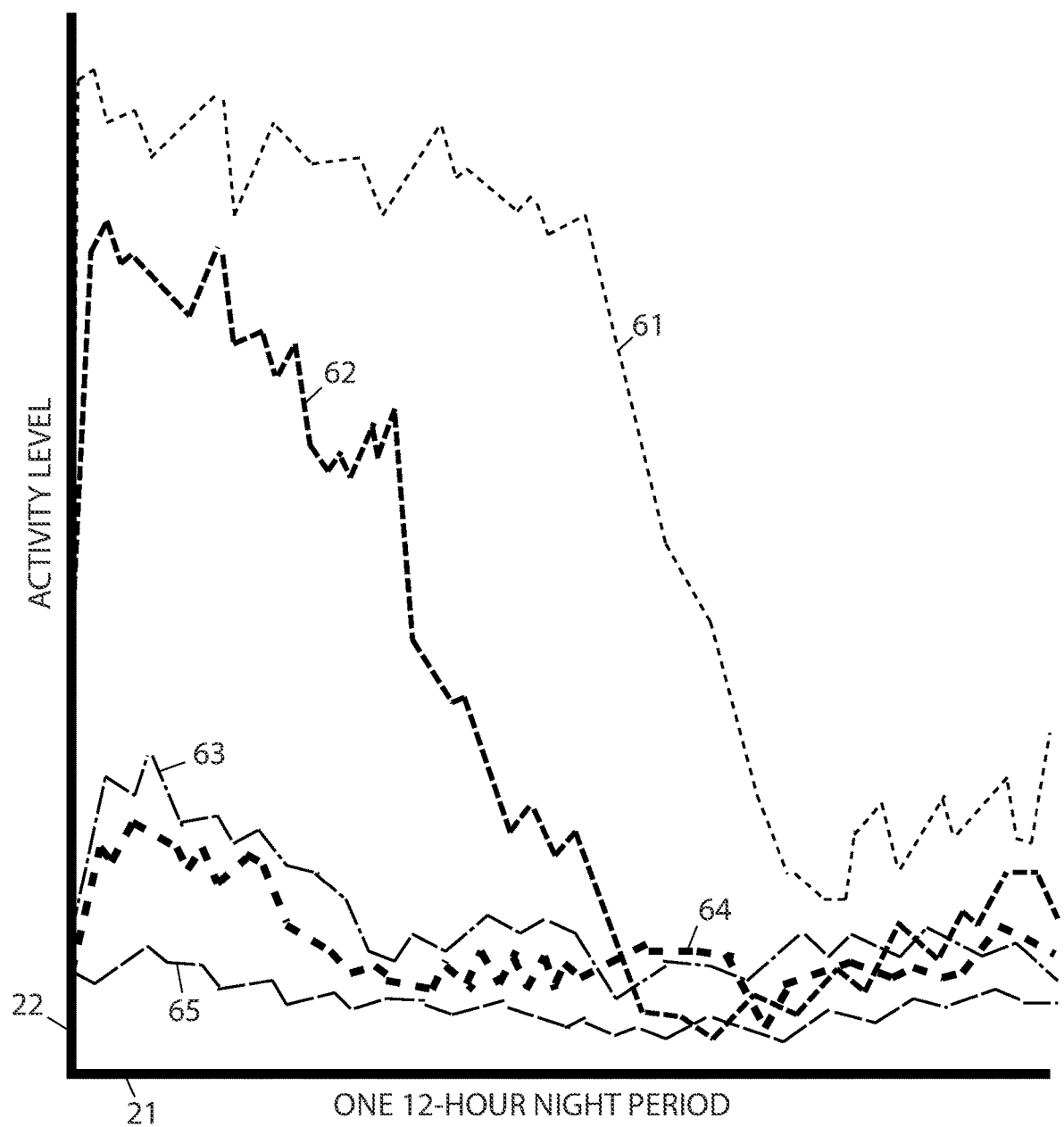
FIG. 3 shows actual measured nighttime activity curves from one study.

FIG. 3 shows five exemplary activity curves for mice in a vivarium induced with MS. The horizontal axis, 21, covers one 12-hour night period. The vertical axis, 22, is activity level. Full scale is 180 mm/sec, as a peak movement speed of the animal, in a time window. Exemplary time windows are 10 minute, 15 minutes, 1 to 30 minutes, 2 to 30 minutes, 3 to 30 minutes, 5 to 30 minutes, 5 to 20 minutes, or another range. Embodiments are claimed for data collection repeated at these time intervals during the night. Graph 61 is an average of activity over multiple days during a Baseline period. Graph 62 is average of activity over multiple days during a Prodromal period. Day 0 is Onset. Graph 65 is an average of activity over multiple days during initial treatment days 0 to 7. Graph 63 is an average of activity during treatment days 7 to 14. Graph 64 is an average of activity during final treatment days 14 to 21. For these graphs, treatment was saline: the naïve vehicle. Here, treatment days include both recovery and steady state. These graphs shown, 61 to 65, are averages for one animal over multiple days. Standard deviations are not shown. Similar graphs may be either be averages for a single animal over the days described, or may be for all animals in the cohort over the days described. Because graphs 63, 64 and 65 each average 7 day periods, these graphs do not show progress through Recovery into Steady State.

What the five graphs 61 to 65 do show in FIG. 3 is that animal activity is highest just after the start of the night, and then lower later in the night. These graphs are not available in the prior art due to the lack of continual monitoring of all animals in a cohort during all hours of the night. Note that at night, visible light (visible to the animals) is off or very dim. To measure these animal activities, infrared (IR) light and an IR sensitive video camera are used on every cage. Graphs 61, 62 and 63 are used again in FIGS. 5, 6, and 7 respectively.

Note that the sicker the animal, the lower their initial activity level. Note also that the sicker the animal the larger its activity-drop. For example, the largest negative slope location, in time, is latest for graph 61, then less for graph 62, then less again for graph 63, then 64, and finally graph 65. Note also, that the total activity for the animal, such as can be measured by the area under a curve for a time interval, also drops, the sicker the animal. Note also, that the sicker the animal, the rapid activity-drop is the sooner after the start of the night. Embodiments are claimed that detect, using curve fitting, each one or any combination of the observations described in this paragraph and visible in FIG. 3. In graphs 65 the animal is so sick that its activity all night is barely above its baseline. Also of interest in these graphs is the observation is that the nocturnal activity goes up slightly during latest part of the night, for all sickness levels.

A summary of animal sickness in general is visible in FIG. 3. This interpretation follows. Graph 61 shows exemplary healthy animal or animals. These animals have not been induced with a disease, such as MS, and so are "normal." Graph 62 shows less healthy, that is, sicker animals than graph 61, Graph 65 shows the sickest animals. Graphs 63 and 64 show animals healthier than graph 65 and sicker than graph 62.

Figure 4:
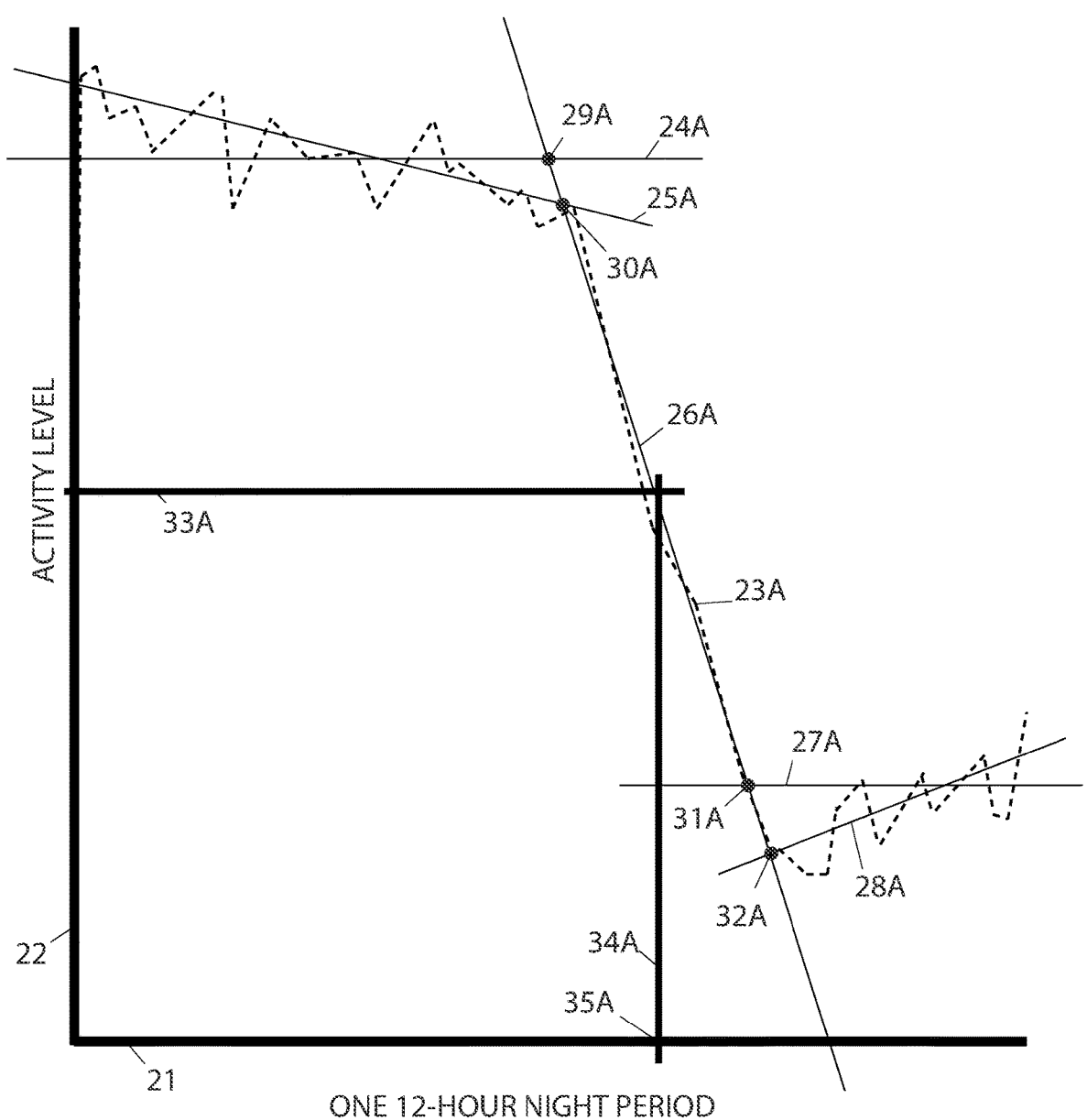
FIG. 4 shows a first exemplary identification of three activity periods in one night.

Turning now to FIG. 4 we see aspects of key embodiments. The horizontal axis 21 is time over one 12-hour night period. The graphs may be measured activity level for one animal for one night, or an average for one animal over more than one night, or averages for more than one animal. The vertical axis 22 is activity level. Dotted line graph 23A is a copy of graph 61 in FIG. 3. Three time periods for graph 23A are identified in steps of methods of embodiments.

For convenience, we name these three periods, "high-activity period," "activity-drop period," and "low-activity period." These three periods are time sequential. They may or may not be contiguous and may or may not cover the entire 12-hour night. However, it is convenient for non-limiting discussion to think of them as both contiguous and starting when the night starts. The high-activity period is shown by curve-fit lines 24A or 25A. The activity-drop period is shown by curve-fit line 26A. The low-activity period is shown by curve-fit lines 27A and 28A. The difference between 24A and 25A is that 24A is a curve-fit of the high-activity period with a fixed, scalar activity level while 25A is a curve-fit that also has a slope. These two lines, 24A and 25A may be best-fits of the high-activity period for the actual graph data, 23A. Similarly, the difference between 27A and 28A is that 27A is a curve-fit of the low-activity period with a fixed, scalar activity level while 28A is a curve-fit that also has a slope. These two lines, 27A and 28A may be best-fits of the low-activity period for the actual graph data, 23A. Line 26A is a best-fit for the activity-drop period; it always has a negative slope.

Dot 29A is the intercept between lines 24A and 26A. If line 24A is used, this dot 29A the boundary between the high-activity period and the activity-drop period. Dot 30A is the intercept between lines 25A and 26A. If line 25A is used, this dot 30A the boundary between the high-activity period and the activity-drop period.

Dot 31A is the intercept between lines 27A and 26A. If line 27A is used, this dot 31A the boundary between the activity-drop period and the low-activity period. Dot 32A is the intercept between lines 28A and 26A. If line 28A is used, this dot 32A the boundary between the activity-drop period and the low-activity period.

Line 26A has a midpoint. Such a midpoint may be computed as half way between (either 29A or 30A) and (either 31A or 32A). The "half way" may be based on either time or activity level, or both. Such a midpoint may also be a point of inflection of line26A if line 26A is modeled as a non-straight curve with a point of inflection. Such a midpoint may also be a point of steepest slope of line 26A if line 26A is modeled as a non-straight curve. A midpoint is shown as the intersection of line 33A and 34A. This midpoint is key to method steps of embodiments. This midpoint has a time, shown as 35A. It also has an activity level scalar, shown as 33A.

There are multiple ways to compute lines 24A, 25A, 26A, 27A and 28A. Most such computations are based on a best-fit. Multiple best-fit algorithms are known in the art, such as least-squares-fit, others described herein, and other curve fitting algorithms known in the art. Curve fitting may involve interpolations, averaging, or smoothing. Regression analysis may be used. Curve fitting may use polynomials or splines. Best-fit may use LASSO or Ridge Regression. Curve fitting may be based on confidence factors. Curve fitting may be subject to limits and may eliminate outlier points. Algorithms such as RANSAC may be used for both curve detection and confidence. Computational techniques for computing lines 24A, 25A, 26A, 27A and 28A may be closed length or iterative. The goal of such curve fitting, for some embodiments is to optimize curve 26A in order to determine points 35A and value 33A with quantitative consistency.

We describe two methods of finding lines 24A, 25A, 26A, 27A and 28A. First, typically, either the line set 24A, 26A and 27A will be used, or line set 25A, 26A and 28A. However, other combinations are possible. Set 24A, 26A and 27A is simpler because 24A and 27A are restricted to horizontal lines. That is, 24A is a scalar "high-activity" value and 27A is a scalar "low-activity" value. Line 26A is then a best-fit between points 29A and 31A. A starting point for curves 24A and 27A is to average an activity level a fixed amount of time from the start of the night (or other time period) and the end of the night (or other time period), respectively. Such times may be one hour, two hours, three hours, four hours, or five hours. Such times may in the range of one to five hours. Given such an initial value determination of line 26A is then an iteration that creates a best-fit of lines 24A, 26A and 27A, although weighting the fit of 26A higher is preferred. Only a single iteration may be used. Using line set 25A, 26A and 28A is more complex because now the slopes of lines 25A and 28A are also part of the best-fit computations. However, this line set is preferred over the simpler set. Numerous best-fit bit algorithms are known in the art. No limitations are placed on best-fit algorithms by these descriptions. Once line 26A has been determined, then a midpoint of 26A is determined, as described above. This midpoint determines time 35A and value 33A. Time 35A or value 33A is the result and purpose of this discussion with respect to FIG. 4, in embodiments.

It is worth noting that a simple midpoint of line 26A is about the same, in FIG. 4, using either point pair 29A and 32A or point pair 30A and 31A.

In FIG. 4, and in some embodiments and claims, we refer to three periods or regions, a "high-activity period," an "activity-drop period," and a "low-activity period." However, in some embodiments one of these three periods may be a zero length period. In particular, the activity-drop period may have zero length with respect to curve fitting. In such a case, any line fitting through this period must be vertical. In another embodiment, the low-activity period may be zero length. In such a case, any line fitting through this period is horizontal, taking a value equal to the value at the end of the activity-drop period. Note that it is possible, in the extreme, to have only two activity levels measured during the night, one corresponding to the activity in the high-activity period and the other corresponding to the activity in the low-activity period, or the activity-drop period.

It is not necessary that the low-activity period extend to the end of the night. In fact, as discussed elsewhere herein, it is advantageous to not include activity during some time at the end of the night. The low-activity period may extend, for example, to only a minimum of activity during the night, or to a fixed time. In addition, the three time periods, "high-activity period," "activity-drop period," and "low-activity period," need not be contiguous, only sequential. The high-activity period need not start at the beginning of the night; however, in a preferred embodiment it starts close to the start of the night.

Figure 5:
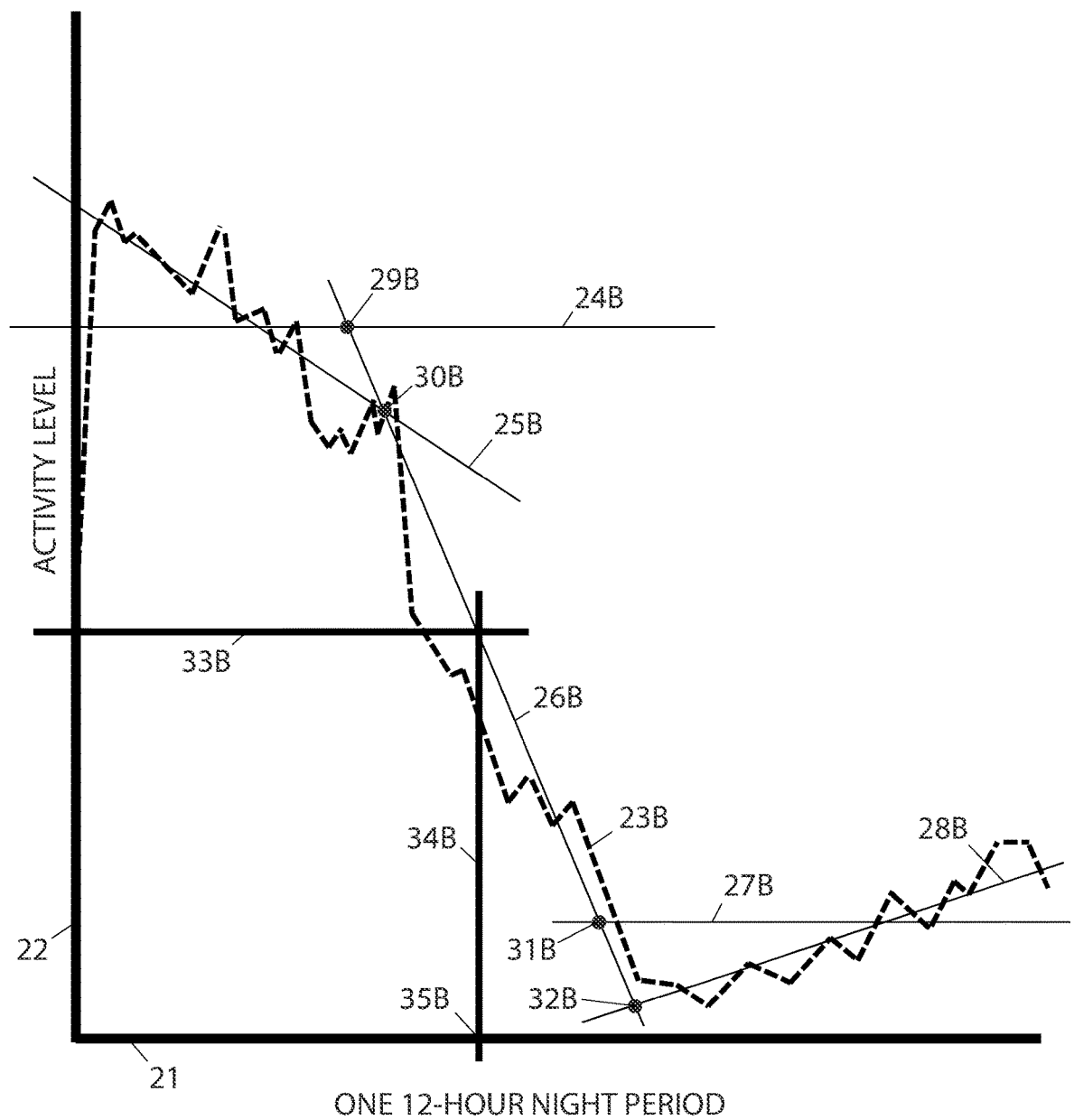
FIG. 5 shows a second exemplary identification of three activity periods in one night

FIG. 5 is similar to FIG. 4, except that the data graph is graph 62 in FIG. 3 instead of graph 61. This graph is shown as 23B in FIG. 5. As in FIG. 4, the horizontal and vertical axes are 21 and 22, respectively. All elements 23B, 24B, 25B, 26B, 27B, 28B, 29B, 30B, 31B, 32B, 33B, 34B and 35B correspond to elements 23A, 24A, 25A, 26A, 27A, 28A, 29A, 30A, 31A, 32A, 33A, 34A and 35A in FIG. 4. That is, curve fitting is used to optimize the location of line 26B, which in turn determines time 35B and value 33B.

Figure 6:
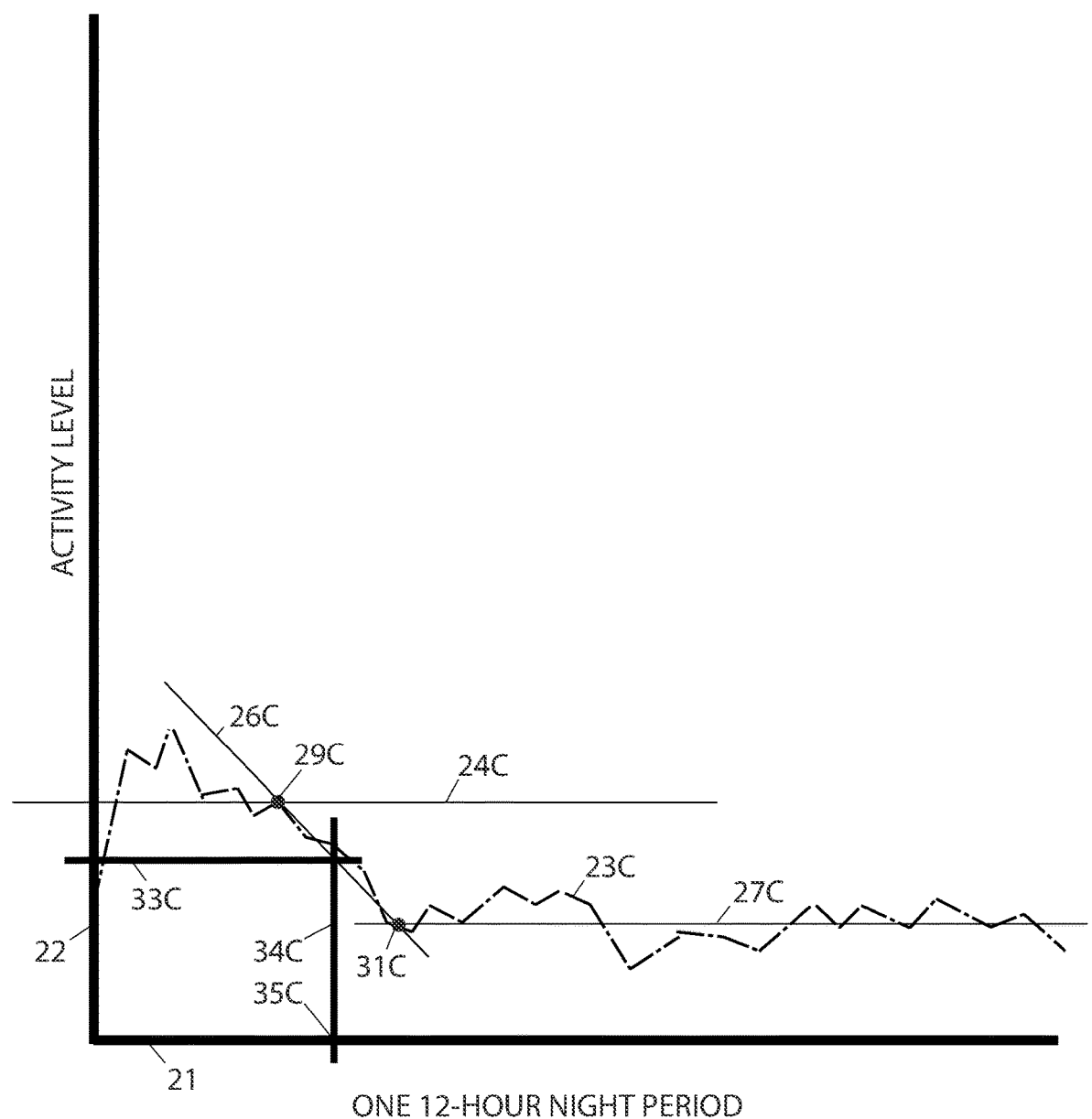
FIG. 6 shows a third exemplary identification of three activity periods in one night.

FIG. 6 is similar to FIG. 4, except that the data graph is graphs 63 in FIG. 3 instead of graph 61. This graph is shown as 23C in FIG. 6. As in FIG. 4, the horizontal and vertical axes are 21 and 22, respectively. All elements 23C, 24C, 25C, 26C, 27C, 28C, 29C, 30C, 31C, 32C, 33C, 34C and 35C correspond to elements 23A, 24A, 25A, 26A, 27A, 28A, 29A, 30A, 31A, 32A, 33A, 34A and 35A in FIG. 4. That is, curve fitting is used to optimize the location of line 26C, which in turn determines time 35C and value 33C.

Considering point 35A, 35B, and 35C in FIGS. 4, 5, and 6 respectively, note that 35A is the latest in the night, 35B is earlier in the night, and 35C is yet earlier in the night.

Whatever curve fit methods and midpoint methods are used for one graph should usually be used for other graphs. That is, the same methods should be used for BASELINE, HEALTH DROP, PRODROMAL, ONSET DROP, RECOVERY AND STEADY STATE health periods of a mouse, cohort or study group.

One embodiment comprises computing a time 35, as shown by example times 35A, 35B and 3C, in FIGS. 4, 5 and 6 respectively, for each animal in a cohort, each night. These times will generally decrease as an animal gets sicker and increase as an animal gets healthier. These times may be used to predict a future course, future sickness, future health, future outcome, or event of an animal, including efficacy or death. As another example, remaining time to ONSET may be predicted. As yet another example, an embodiment predicts how most sick an animal will get in ONSET. As yet another example, an embodiment predicts the level of health of the animal in STEADY STATE. We refer to the goals or outputs of these embodiments as predictions.

An embodiment finds a monotonic relationship between such times 35 or 33 and a desired prediction by testing and using regression analysis or a best-fit algorithm, such as a least-squares fit, or another method, such as RANSAC, or another method, such as Monte Carlo testing of variations, or another method, such as simulated annealing, to determine the monotonic relationship between times 35 or 33 and the desired prediction. Given this determined relationship, then times 35 or value 33 as measured during a study, may be used, in embodiments, to make the desired prediction.

Methods applied in embodiments, such as shown in FIGS. 4 through 6, may be used to measure animal health after ONSET, such as during STEADY STATE. Such measurements of two or more cohorts may then be used to measure the efficacy of a treatment. Some embodiments compute health as a percent of the animal's health during its BASELINE period. STEADY STATE may be a predetermined time period after ONSET, or may be determined by another method, such as observing that an animal's health is no longer changing by more than a threshold, or has reached a minimum threshold of health. An efficacy determination or computation may be responsive to an average health or may be responsive to a worst-case health.

Figure 7:
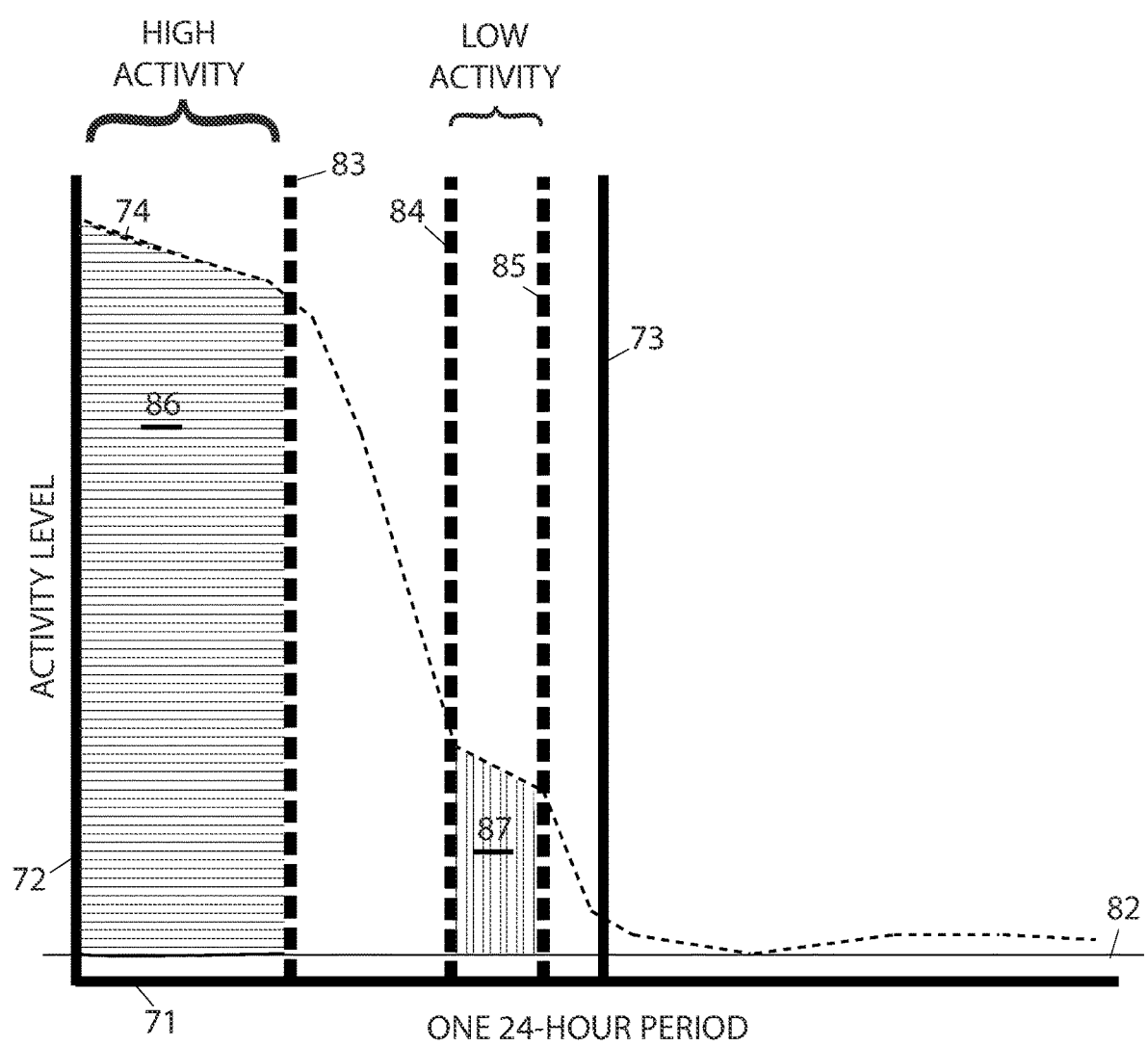
FIG. 7 shows overlaid exemplary activity periods during four exemplary different sicknesses.

Turning now to FIG. 7, we examples of use of area or areas under curves for computing an activity value. The horizontal time axis 24 shows one 24-hour period; the vertical axis 72 shows a measured, or measured and computed, scalar activity level; curve 74 shows one activity graph for one animal. For discussion in this exemplary Figure, curve 74 represents activity measurements of an animal during its BASELINE period. In this Figure, we compute a new baseline 82 that is the minimum activity of the animal. It is understood that when we discuss "area under a curve" we are referring to integration of the curve if continuous or a summation if the data are discreet points. In general, the terms "curve" and "graph" are interchangeable and refer to the data so represented, in the context of area under curves. Continuous curves may be created from discreet points and including smoothing or averaging, including running averaging.

In this Figure, two areas are shown, 86 and 87. It is first necessary to create two time periods during the night: a "high-activity period," and a "low-activity period." Details of creating such time periods during the night, for a particular graph, are described elsewhere herein. Time periods may be fixed or they may be variable. They may be the same for all activity graphs, of either an animal through time animal, or multiple animals across as study. A preferred embodiment computes these time periods uniquely for every animal every night. The high-activity period in this exemplary Figure is shown from the start of the night 72 to vertical line 83. The low-activity period is shown from vertical line 84 to vertical line 85. These two time periods do not need to be contiguous, or start or end at the start or end of the night. However, they do need to be sequential in time.

We describe three basic embodiments to compute a nightly activity value using areas under curves, and then we describe variations on these embodiments. For the first such method the nightly activity value is simply area 86, that is, the area between curve 74 and baseline 82 during the high-activity period. For the second and third such methods, area 87 is also determined; that is, the area between curve 74 and baseline 82 during the low-activity period. Given the numerical areas 86 and 87 we now either subtract area 87 from area 86 (method two) or we divide area 86 by area 87 (method three). Note that baseline 82 may be valued other than minimum activity during the night, including zero. In some embodiments when computing nightly activity values for different curves using methods two and three that the ratio of the high-activity time length to the low-activity time length stays constant.

Additional embodiments are variations on the above three computational methods for a nightly activity value. We may wish to normalize the values computed above by comparing to the activity level of the same animal during that animal's BASELINE period. We then either subtract a preliminary from that Baseline value or divide the preliminary activity level by that Baseline value to accomplish such normalization and generate a final activity level or value.

In general, the healthier the animal, the larger area 86. For relatively healthy animals, the peak activity level will be fairly constant. However, the length of that high-activity will vary according to animal health. That is, line 83 will be more to the left for less healthy animals and more to the right for more healthy animals. When an animal is sicker, the peak activity level will also decrease. Thus, approximately, starting with a very healthy animal, as it gets steadily sicker, first area 86 will decrease in width, and then decrease in height. The width of the low-activity period may vary significantly. However, the area 87 is nearly always larger for healthier animals and smaller for sicker animals.

Figure 8:
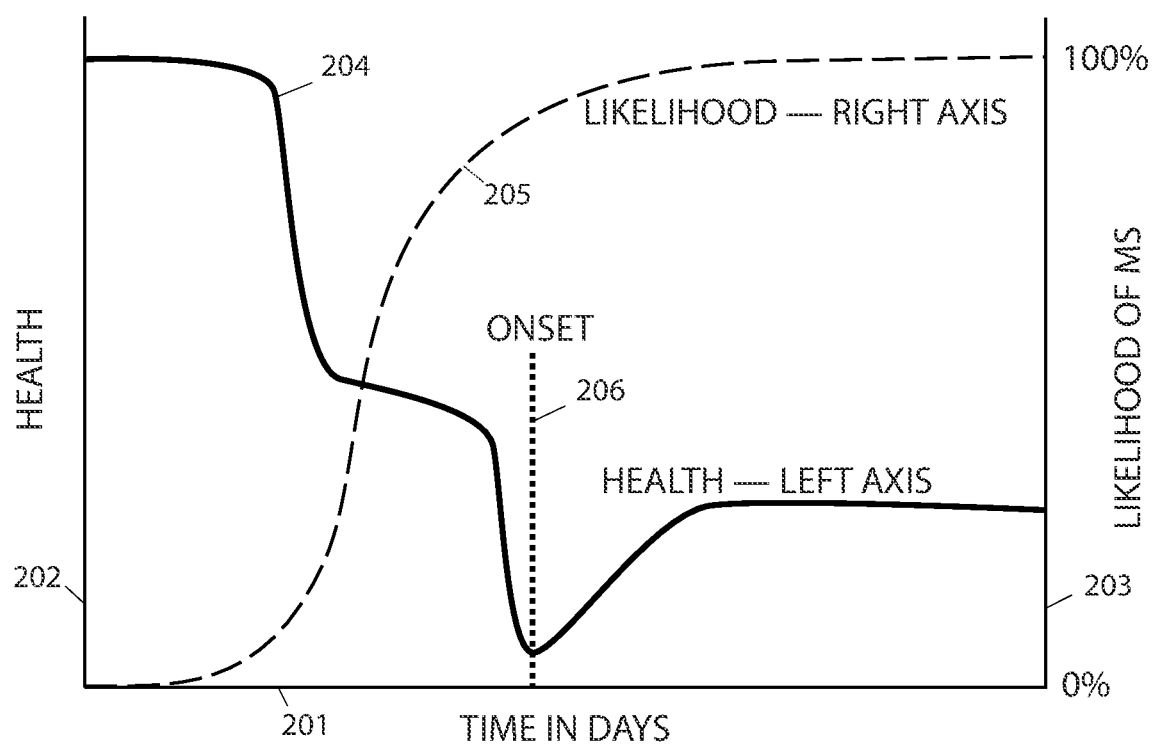
FIG. 8 shows an exemplary MS health detection or prediction function.

Turning now to FIG. 8, we see an MS Health Detection or Prediction Function, 205. Such a curve may be, without limitation, a likelihood of early MS detection; predicted severity, likelihood of Onset, predicted efficacy, efficacy, or another prediction or derived computation. For convenience, we will now refer to this curve, 205, as a likelihood of an animal becoming sick with MS, where "sick" is defined by some criteria. Such likelihood is computed from health measurements taken or computed, for example, each night, based on a plurality of activity measurements of the animal that night. In this Figure, such animal health or animal activity value is shown as curve 204. Time is on the horizontal axis, 201. Health, in arbitrary units, is shown on the left axis, 202. The left vertical axis is used for health curve 204. A likelihood of MS, as a percent predictor, is shown on the right vertical axis, 203, for curve 205. Note that although this chart uses days as the horizontal axis, 201, an exemplary likelihood function, shown in curve 205, is not directly a function of time, but rather a function of health, curve 204. Thus, this Figure may be accurate for a single animal whose health curve is 204. However, most likely for a different animal, with a different health curve 204, the shape of likelihood curve 205 will appear different, even if the same function is used to compute the likelihood. Onset 206 is shown here for convenience. This Figure is schematic only. Actual curves may be significantly different. Note that the likelihood curve 205 as shown in this Figure is for an animal that definitely gets MS, as the likelihood reaches 100% on the right of the graph. The likelihood, shown as or near zero, on the left side of the graph may not be realistic as there may be insufficient data yet collected to make a credible determination. A prediction, such as curve 205, may be used to make an enrollment decision, perhaps a predicted enrollment or retroactive enrollment. Such a use of curve 205 is expressly claimed as an embodiment. In some embodiments, a curve further includes a confidence, not shown.

Embodiments for the early detection of MS generate a set of scalars, with corresponding optional confidences, over time. Such an example is curve 205 in FIG. 8. Such scalars may be normalized to generate a probability in the range of 0 to 100%, however such normalization is not mandatory. Such normalization may or may not be part of a claimed embodiment. Thus, "detection" of MS may be a series of scalars, with optional confidence, in arbitrary units. Such arbitrary units are appropriate because the exact definitions of MS may be different for different purposes or different studies. "Confidence" may or may not be a scalar. It may, for example, be a distribution function.

Embodiments may use a computed predictor, such as shown as curve 205 in FIG. 8, to predict ultimate health of the animal. Embodiments may use a computed predictor, such as shown as curve 205 in FIG. 8, to measure efficacy of treatment. For example, the right vertical axis in FIG. 8 might be "Efficacy of Treatment." 100% might be defined as an animal achieving a health during STEADY STATE equal to its health during BASELINE, or some other criteria, such as at least 50% as healthy, or at last 30% as healthy. In some embodiments efficacy of treatment may be relative to no treatment or relative to a standard of care or relative to another treatment. Thus, this curve may be so normalized. In these cases, it is necessary to compare averages or aggregates of one cohort against another cohort. Comparison to no treatment or a standard of treatment is not shown in FIG. 8, but is well known in the art.

Figure 9:
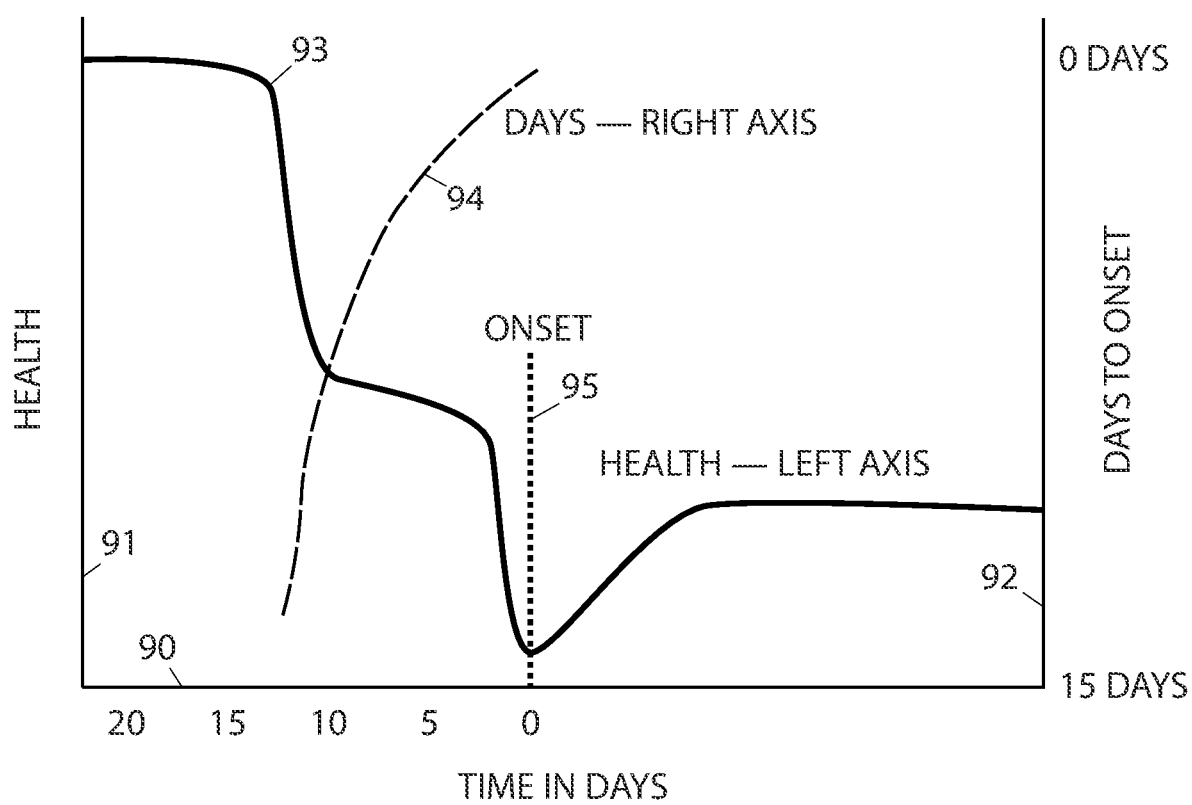
FIG. 9 shows a second exemplary MS health detection or prediction function.

Turning now to FIG. 9, we see an MS Health Detection or Prediction Function, 94. Such a curve may be, without limitation, a prediction of days to Onset of MS, a prediction of an animal getting sick, a predicted disease severity, predicted or actual efficacy or another prediction or derived computation. For convenience, we will now refer to this curve, 94, as a predictor of days to Onset of disease, where Onset is defined for a study as meeting some criteria. Such a predictor is computed from health measurements taken or computed, for example, each night, based on a plurality of activity measurements of the animal that night. In this Figure, such animal health is shown as curve 93. Time is on the horizontal axis, 90. Note that for this Figure, day zero is set to Onset 95, which is a usage and presentation common in the art. The units 20 through zero shown on the horizontal axis may be viewed as negative numbers, if that is convenient. Health, in arbitrary units, is shown on the left axis, 91. This axis is used for health curve 93. Days to Onset predictor, is shown on the right axis, 92, for curve 94. Note that curve 94 is shown in units of "days remaining" as of the date the prediction is made. Other units could be used for a predictor. Note if the predictor were perfect, for this Figure, curve 94 would a straight-line from 15 days on the horizontal axis to zero days on both the bottom and right axes. Since curve 94 is not straight we observe that the predictor, in this example, is not perfect.

Note that although this chart uses days as the horizontal axis, 90, a predictor function, whose value is shown in curve 94, is not directly a function of time, but rather a function of health curve 93. Thus, this Figure may be accurate for a single animal whose health curve is 93. However, most likely for a different animal, with a different health curve 93, the predictor curve 94 will show as different, even if the same function is used to compute the predictor. Thus, the predictor 94 is typically computed as function of curve 93, not time. Onset 95 is shown as the goal of the predictor, in this example, to predict this date accurately. Note that since actual Onset is not known until Day Zero, in this Figure, the health as shown as curve 93 may only be aligned with the units shown in the horizontal axis at or after Onset. This Figure is schematic only. Actual curves may be significantly different. Note that the predictor, 94 as shown in this Figure, is for an animal that reaches Onset. A prediction, such as curve 94, may be used to make an enrollment decision, perhaps a predicted enrollment or retroactive enrollment. Such a use of curve 94 is expressly claimed as an embodiment. In some embodiments, a curve further includes a confidence, not shown.

Figure 10:
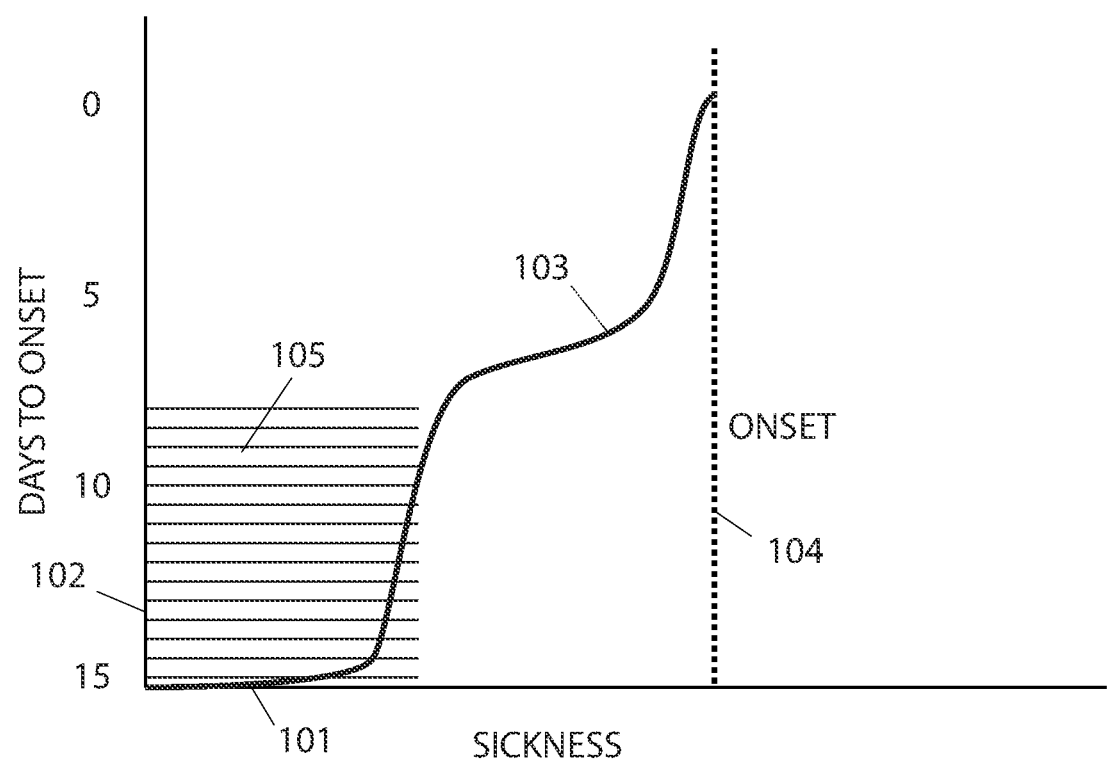
FIG. 10 shows a third exemplary MS health detection or prediction function as a function of sickness.

Turning now to FIG. 10, we see another predictor function 103 that uses the left vertical axis 102 for its scale. Unlike FIGS. 8 and 9, the horizontal axis 101 is now sickness, increasing towards the right. In general, description and embodiments above for an Onset predictor apply to the curve 103 shown in this Figure. This Figure also shows a low confidence area, 105, where the predictor function 103 is probably not useful. In this example, the animal is not yet sick enough to make a usefully accurate prediction. Embodiments generating such a predictor function may have steps to create or use such an area as 105, or may not generate a predictor until an animal meets some criteria, such as a threshold level of sickness or a threshold confidence. Once an animal has reached Onset, 104, the days to Onset predictor stops.

Figure 11:
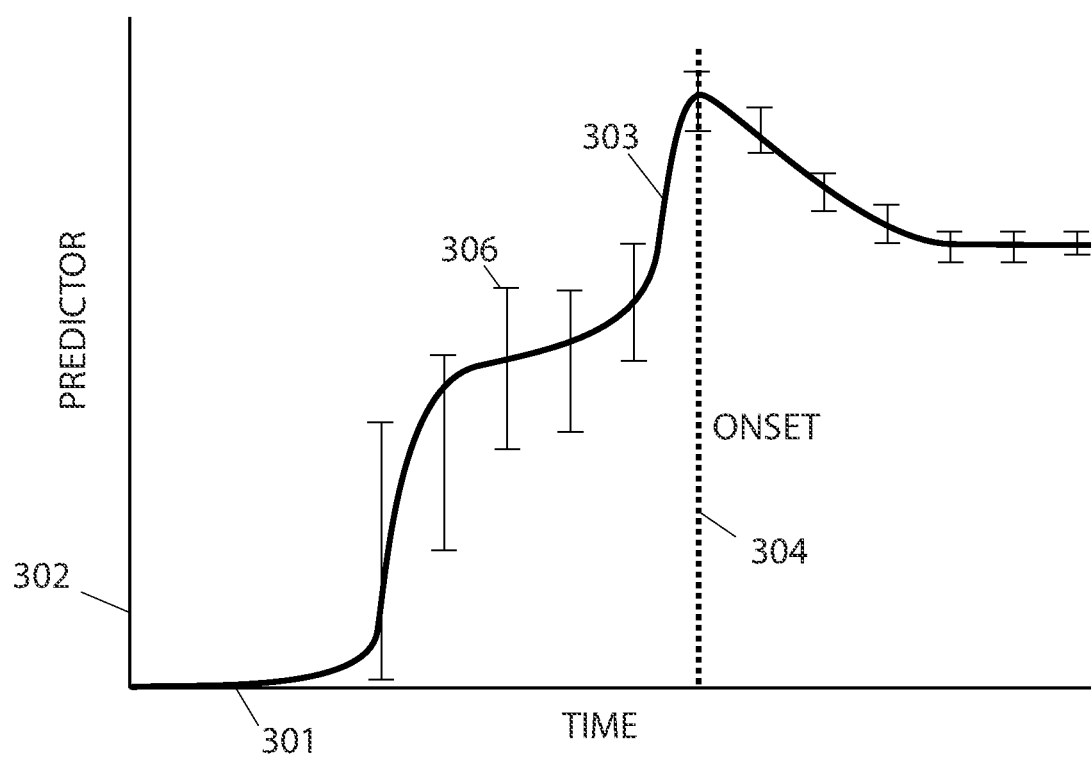
FIG. 11 shows a fourth exemplary MS health detection or prediction function as a function of time, with confidence bars.

Turning now to FIG. 11, we see another predictor function, 303. The horizontal axis 301 is time. The vertical axis 302 is the units of the predictor function 303. Bars 306 show confidence or range limits for the values on predictor curve 303. Such bars might represent one standard deviation (sigma) on a Normal probability distribution, a range showing 95% confidence, or may be some other unit. Note that in the exemplary predictor function shown, the possible error is high near the start and lower at the end. That is, the confidence is low at the start and higher at the end. Exemplary curve 303 might be a probability of getting a disease or not getting a disease, a measure of a treatment efficacy, predicted disease severity, or another computed metric of animal health derived from observed activity data. The Onset time 304 is provided for convenience. It would not apply to all predictors. Note that predictor functions may not be monotonic.

Figure 12:
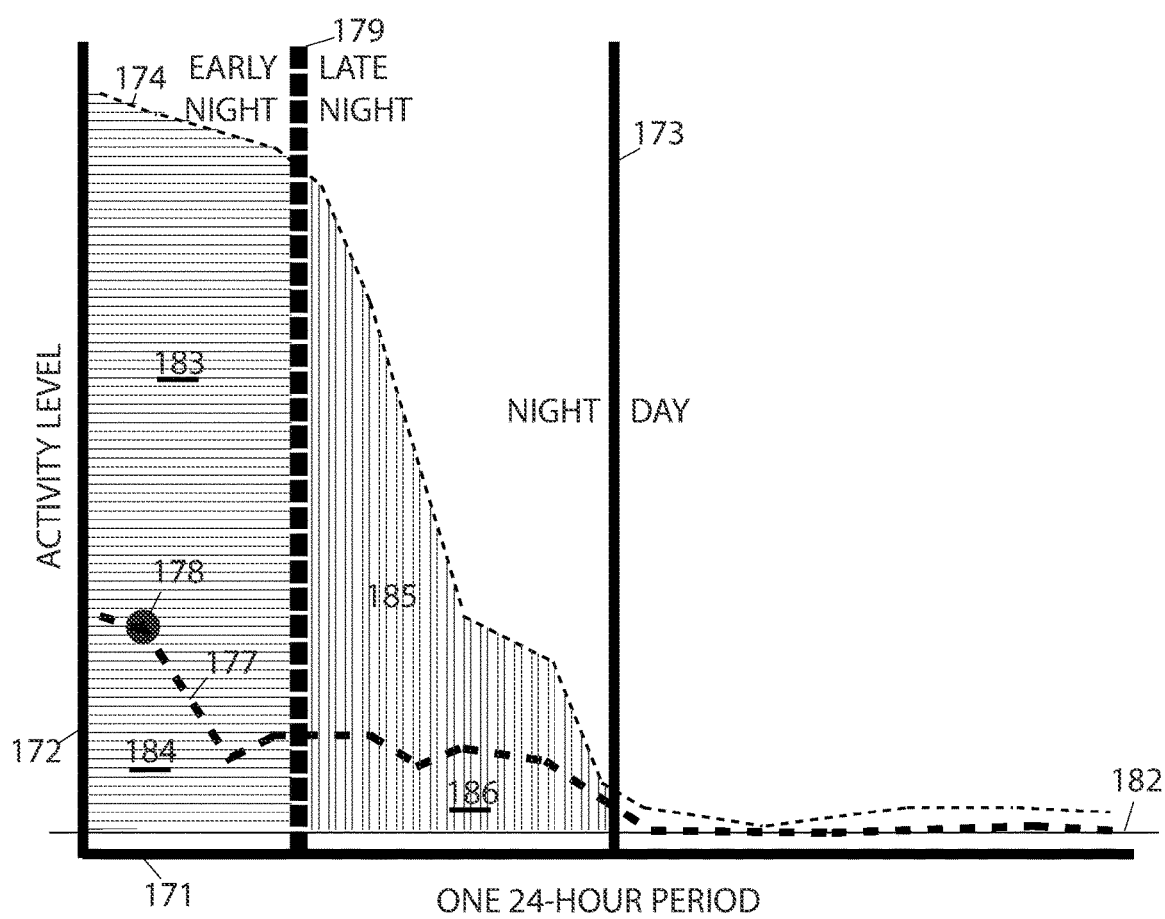
FIG. 12 shows an example of an embodiment using areas under activity curves to compute an activity level.

Turning now to FIG. 12, we see a variation on FIG. 7, showing some different embodiments using areas under curves. Similar to FIG. 7 the horizontal axis 171 in time, for one 24-hour period. The vertical axis 172 is measured activity level, typically of one animal per graph, typically measured repeatedly and continually throughout a night, as shown by continuous graphs 174 and 177. Line 173 shows the partition between night and day; it is clear that the animals, such as mice, are nocturnal. Embodiments partition the night into time regions. There may be three such regions: a high-activity region, an activity-drop region, and a low-activity region. Such three-region portioning is described elsewhere herein and not shown in this Figure. There may be two non-contiguous time regions, such as a high-activity region and a low-activity region. Such two separate region portioning is described elsewhere herein and not shown in this Figure. This Figure shows a simple portioning of the night into two time regions: "early night" and "late night." Such time regions need to be sequential, but they do not need to be contiguous and do not need to start and end respectively at the start and end of the night, as shown in this simple and exemplary partitioning. This Figure shows a healthy animal in graph 174 and a sick animal in graph 177.

There are multiple embodiments to compute both "absolute" health and relative health from the areas shown: 183, 184, 185 and 186. We now use the reference designators to refer to their associated areas: Absolute health may be areas under the curve such as 183+184 or 183+184+185+186 for curve 174; 184 or 184+186 for curve 177. Health may be relative such as 183/184, or (183+185)/(184+186). All areas may be adjusted by subtracting a baseline activity level, such as line 182. The partition line 179 may move dependent upon one or more curves. For example, this line is well positioned in the Figure at the point of inflection for curve 174 from high-activity to an activity-drop. Whereas, for curve 177 the partition line should be moved to an earlier time at the inflection point 178, prior to computing areas under curve 177. All areas, or computations from areas, may be modified by subtracting any relevant Baseline, such as an animal's health pre-induction. All areas, or computation from areas, may be normalized to a reference computation or health, such as an animal's health pre-induction, or a control group. All areas, or computation from areas, may be normalized or converted to industry standard units of health or sickness.

Continuing with FIG. 12, curves such as 174 and 177 may be from data collected from one individual animal for one night, or they may be averages or summations ("aggregates"). One such average is for multiple animals in a cohort over the same night: data generally collected or measured in parallel. Another such average is for one animal for multiple nights. Such averaging may be appropriate for periods such as a pre-induction Baseline period, or a relatively constant recovery period. Such averaging may be used during Prodromal, although is usually not a preferred embodiment. Another such average is for both multiple animals and multiple nights. In addition, some embodiments average activity scalars after the activity scalars are computed from the activity graphs. Again, the averaging may be for one night, multiple animals; or one animal, multiple nights; or multiple animals, multiple nights. In addition, some embodiments average after a function is applied to the datasets. Such functions may be to predict or detect MS or another disease, or to measure efficacy of treatment, or to predict severity of MS or another disease, or to detect or predict a condition, such as death; or to predict or measure relapse, or another function. Averages may be plotted or graphed over time. Curve fitting may be used on such graphed averages to generate a prediction or detection, or compute an efficacy.

Curves such as 174 and 177 in FIG. 12 may be used to detect a transition from one time period to another, such as the twelve named time periods or events in FIG. 1. Curves such as 174 and 177 in FIG. 12 may be used to measure health or relative health between any two of the eleven named time periods or events in FIG. 1. Curves such as 174 and 177 in FIG. 12 may be used to predict a transition time such as between any two adjacent named time periods or events in FIG. 1

FIG. 12 can be used for other purposes, such as between an Onset and another timer period, or time periods before or after Onset or before or after treatment.

Novelty of embodiments focus on these nexus elements: in an animal study in a vivarium: (1) multiple activity measurements during a night to construct a continuous or discreet graph, such any of 61 through 65 in FIG. 3; (2) computing an activity scalar (with an optional confidence scalar) responsive to the graphs, using a three-time-region with curve fitting, a LASSO analysis, a Fourier on a circle analysis; or an area-under-a-curve analysis; (3) collecting these scalars from sequential nights into a dataset; (4) applying a known function to the dataset to obtain a result. Such a result might be early detection or prediction, such as of disease, or a severity of a disease, or death; or it might be a measure of a treatment efficacy; or it might be for a different result. The function in (4) above is not magic. It is easily computed by comparing the results of steps (1) through (3) above using various test functions against a reference. Such a reference might be an actual (after the data is collected) event, such as a disease, a severity, an outcome, or death. Such a reference might be a different cohort or known data in the art. Such a reference might be no treatment (or a naïve vehicle) or a current best practice. Methods such as curve fitting, regression analysis, LASSO, RANSAC, Mont Carlo, simulated annealing and others known in the art maybe used to identify a relationship and fine tune such a function in (4), above. In two simple embodiments, such a function may be a multiplicative constant or multiplication of a linear curve over time. In these two embodiments, the desired result is essentially the collected scalars in (3), offset from a baseline and normalized to either an unit of art, a percentage, or to some baseline activity levels, such as healthy animals, a control group, or an animal's activity prior to induction.

An additional novelty of some embodiments is collecting activity measurements, in (1), above, for at least one individual animal housed in its home cage with other animals. This is particularly challenging because animals must be identified uniquely and reliably in the dark. One such technique is to track a known animal's movement in its cage, such as using video analytics. An animal may become known using a short-range RFID when that animal alone is near an RFID receiver. An animal may become known by its weight on a scale, where its weight is unique for all the animals in the cage. An animal may be identified or become known by reading a code marked on its tail.

In another embodiment, measurements and method steps performed made prior to Onset may be used to determine if Onset will occur or not. That is, whether or not the animal will get, "sick," as defined by the criteria for Onset. Such determination is valuable for two reasons: (1) Such animals are excluded from enrollment or are evenly distributed into different cohorts, a process called randomization, or (2) Animals are excluded from prophylactic treatment. In yet another embodiment, measurements and method steps performed prior to Onset may be used to predict a severity of sickness for an animal. In both embodiments above, the results may be used for randomization.

Embodiments are specifically claimed for methods described and then applied to achieve randomization. That is, a described method is performed and then the outcome of that method is used, at least in part, to assign an animal to a cohort. (" . . . assigning to a cohort responsive to a value from a previous step;") Embodiments are specifically claimed for methods described and then applied to a decision to enroll or not enroll an animal.

In another embodiment, measurements made prior to Onset may be used to predict the ultimate health of the animal; that is, how sick the animal will get. Typically, such ultimate health is determined by measurements of the animal taken in the Steady State period.

Computed animal health values, including but not limited to early detection of disease, measuring efficacy of treatment, collecting data, and predicting severity may be described in the specification, shown in drawings, or claimed in claims or embodiments, without a specific reference to, or responsive to a measured animal health during that animal's Baseline period. In yet another embodiment, all such animal health values are then modified or further computed as a percentage of the animal's Baseline health value. Embodiments include measurements for both single animals and cohorts. Typically, when taking measurements in a cohort, the health of each animal is first computed separately. However, in some embodiments, the percentage computation just described may use an average Baseline health for the cohort rather the Baseline health for each animal, as the denominator. In yet another embodiment, such normalization to each animal's Baseline health may occur in intermediate computations, such as before or in the animal health dataset. Aggregation of data is useful to minimize noise. In yet another embodiment, curves or graphs shown in FIGS. 3 through 10 may be so normalized to each animal's Baseline health prior to use of the graph or the numbers it represents.

Computed animal health values, including but not limited to early detection of disease, measuring efficacy of treatment, collecting data, and predicting severity may be described in the specification, shown in drawings, or claimed in claims or embodiments, without a specific reference to, or responsive to a measured low animal activity of the animal in any period at any time (such as during a day). In yet another embodiment, all animal health values are modified or further computed by subtracting a value responsive to such low animal activity. Embodiments include measurements for both single animals and cohorts. Embodiments include such low animal activity either temporally local, such as during the same night or an adjoining day, or during a different time period, such as Baseline, Onset Drop, Onset, or Recovery. Such measured low animal activity may comprise a minimum activity or an average of minimum activities. Typically, when taking measurements in a cohort, the health of each animal is first computed separately. However, in some embodiments, the subtraction computation just described may use an average Baseline health for the cohort rather the Baseline health for each animal, for the subtraction. In yet another embodiment, such offset to each animal's Baseline health may occur in intermediate computations, such as before or in the animal health dataset. In yet another embodiment, curves or graphs shown in FIGS. 3 through 10 may be so modified responsive to each animal's measured low-activity prior to use of the graph or the numbers it represents. Such modification may occur after data is collected but prior to final analysis. Both normalization and subtraction modifications to measured or computed activity or health may be combined.

In yet another embodiment, computing a scalar value may further include computing an associated confidence. Such a confidence may be a sigma such as related to an expected normal (or, "Gaussian") distribution of the scalar value. Such a confidence may be between zero and one, zero representing "no confidence" and one representing "100% confidence." Such a confidence may be a binary value, essentially indicating if the associated scalar value should be used later, or not. Such a confidence may be a probability distribution curve. Such a confidence may be associated with a non-normal probability distribution curve, such as a Laplace distribution. Such a confidence may be used when aggregating data from multiple animals in a cohort to generate a more inclusive, compressive, meaningful or accurate distribution of probability or confidence of final results.

Some embodiments use Fourier analysis, particularly Fourier analysis on a circle, to generate a scalar with an optional confidence for an animal health for one night. When data is collected for a full 24-hour period, typically shown starting at the start of night, the data is predominantly cyclical, and is thus a good candidate for Fourier analysis. In circular Fourier analysis, a set of discreet transform values is generated. These may be linearly combined using a set of coefficients. The result of such combining is then a nightly activity value. Embodiments using a linear combination of discreet transform values from a circular Fourier transform on measured activity levels to generate a nightly activity value are specifically claimed.

Some embodiments use LASSO (least absolute shrinkage and selection operator) as a method of curve fitting or extracting a scalar (with an optional confidence) from nightly data from one animal. Examples of this, using MATLAB® from MathWords® syntax, is as follows: Using form B=lasso(X,Y), where X is a matrix with N rows, where N is number of samples taken during the night (or a set of samples) and one or more columns represent the value of the sample, such as activity. Thus, X is a discreet representation of the curves shown in FIGS. 4 through 10. Y is a numeric vector of length N, and Y(i) is the response to the one or more column values in row i. For a two-piece piece-wise linear model, lasso may be used twice, once for each linear piece of the data. One example is the two lines (24A or 25A) and 26A from FIG. 4. Another example is the two lines (24A or 24B) and (26A nor 28A) from FIG. 4. Similarly for a three-piece wise linear model, such as shown in FIG. 4 by lines 25A, 26A and 27A. Embodiments using LASSO include more sophisticated applications, such as the form [B, FitInfo]=lasso(X,Y}, where FitInfo includes a confidence, such as described elsewhere herein. Embodiments using LASSO include more sophisticated applications, such as the form [B, FitInfo]=lasso(X,Y, Name, Value}, where FitInfo includes a confidence, such as described elsewhere herein and Name, Value are as described in MATLAB Documentation as of the filing date of this application. Both LASSO and RANSAC are good at removing outlier data.

Key embodiments collect activity data for multiple animals in a cage. In these cases it is necessary to uniquely and reliably identify each animal so that measured activity, such as motion or use of an apparatus, may be attributed to the correct animal. Prior art cannot automatically measure activity for individual animals in a cage with multiple animals. Embodiments wherein the animal is "housed in a cage with multiple animals" are specifically claimed.

Claims are made with respect to "nightly activity" levels. However, in some embodiments, measurements from more than one consecutive night may be averaged. For example, two or three nights may be averaged, and then the stated method steps applied. Alternatively, a "running average" may be computed. Embodiments are specifically claimed for such multi-night averages and such running averages in place of "nightly" measurements.

Embodiments are claimed wherein a terminating condition for collecting animal activity data is any combination of: (1) likelihood of the animal having MS exceeds a likelihood threshold; (2) data collection after induction occurs for at least a number of nights threshold; (3) the animal's health declines below a health threshold; (4) animal health changes less than a change threshold from at least one prior night.

Embodiments are described relating to multiple sclerosis (MS). Embodiments are claimed using the method steps described for immune related diseases in place of MS. Embodiments are claimed using the method steps described for disease in place of MS.

Embodiments are claimed for embodiments requiring a vivarium, requiring animals in a vivarium, requiring multi-housed animals in a vivarium, requiring data collection to be performed in darkness as determined by the animals' light perception, requiring a minimum of two, three, four or five data collection actions per night; requiring at least some data collection to occur in an animal's home cage; requiring data collection to occur only in an animal's home cage; in any combination.

Embodiments are claimed for data collection to optionally include the animal's weight and for embodiments requiring data collection to include the animal's weight. For data collection requiring weight, the animal health detection function must additionally be responsive to the animal weight.

Embodiments are specifically claimed where a broader "curve fitting" step is substituted for specific curve fitting sub-steps described in as-filed claims and embodiments of the specification and drawings.

A confidence value or distribution function may be computed by consideration of variations in any group of source data, curves or graphs that are used for generating an average value, curve or graph. As is known in the art, given a set of values, a confidence may generated such as the complete range, a percent of the complete range, a standard deviation for a Normal distribution, or other distribution. The web page, "List_of probability_distributions" in Wikipedia.org provides such as list. Generating any of these confidence values or distribution curves as part of other embodiments described herein are expressly claimed as embodiments. See FIG. 11 for an exemplary display of one such confidence values.

Embodiments are specifically claimed for devices that execute the methods described or claimed. Embodiments are specifically claimed for systems that execute the methods described or claimed.

Definitions

"Best-fit"—a variety of techniques, including but not limited to: linear fit, least-squares fit, regression or multiple regression analysis, LASSO, RANSAC, piece-wise linear fit, splines including B-splines and cubic spines, and curve-fitting to a predetermined equation. Best-fit may include outliner removal.

"Confidence value" may be a number, such as in the range of zero (no confidence at all) to one (100% confidence); or a sigma for a normal distribution function around the output scalar; or any distribution function, although note that in this general case the "value" may be more complex than a scalar.

"Curve" or "Graph"—a set of data point, either treated discretely or connected so as to produce one or more output values responsive to one or more input values. Such a curve or graph may include averaging or smoothing. It may include aggregated data either over time or over multiple data sources, such as multiple animals or multiple studies.

"Health" and "sickness"—as used herein, unless otherwise clear from the context, are opposites but refer to the same behavior, measure or result. Units used in the art may be significantly different for health and sickness, however. In addition, common baselines for health and sickness may be different. In addition, common normalization for health and sickness values or results may be different.

"Linear combination coefficient set"—a set of coefficients that may be multiplied with a same-sized set of variables, then summed, to generate a scalar. For example: $S=ax+by+cz$; where a, b, are c are the coefficients; x, y, and z are the variables, and S is the scalar result. When a function generates a set of variables, potentially a set with more elements than the number of elements in the linear combination coefficient set, then a subset of variables are used, generally a fixed subset. For some functions, the output variables have a natural order. Most commonly, the variables are then used in order until all the elements in the linear combination coefficient set are used.

"Measuring" and "recording"—may be one or the other, recording may be offsite; may only access the data, rather than record; could have a scenario where a first party hosts the animals, a second party takes the measurements, a third party stores the data, and fourth part does data analysis. We consider taking the measurement and the data analysis to be both together and separately to be embodiments of this invention.

"Metric"—The word, "metric," has two potential meanings, precisely as google provides (as of the filing date): (1) "a system . . . of measurement; (2) metric unit or the metric system." The usage herein is definition (1), unless otherwise clear by the context. In particular, a measurement metric, e.g. "activity-drop metric," is a system of measurement: a measuring method or procedure. Such a procedure may include specific steps including computation steps.

"Multi-housed"—more than one animal housed in a cage, particularly a home cage.

"Night"—a time period perceived by an animal in a study as night. This is commonly when light visible to the animal is turned off. The term, "dark" is also relative to the animal's perception.

Ideal, Ideally, Optimum and Preferred—Use of the words, "ideal," "ideally," "optimum," "optimum," "should" and "preferred," when used in the context of describing this invention, refer specifically a best mode for one or more embodiments for one or more applications of this invention. Such best modes are non-limiting, and may not be the best mode for all embodiments, applications, or implementation technologies, as one trained in the art will appreciate.

All examples are sample embodiments. In particular, the phrase "invention" should be interpreted under all conditions to mean, "an embodiment of this invention." Examples, scenarios, and drawings are non-limiting. The only limitations of this invention are in the claims.

May, Could, Option, Mode, Alternative and Feature—Use of the words, "may," "could," "option," "optional," "mode," "alternative," "typical," "ideal," and "feature," when used in the context of describing this invention, refer specifically to various embodiments of this invention. Described benefits refer only to those embodiments that provide that benefit. All descriptions herein are non-limiting, as one trained in the art appreciates.

Embodiments of this invention explicitly include all combinations and sub-combinations of all features, elements and limitation of all claims. Embodiments of this invention explicitly include all combinations and sub-combinations of all features, elements, examples, embodiments, tables, values, ranges, and drawings in the specification and drawings. Embodiments of this invention explicitly include devices and systems to implement any combination of all methods described in the claims, specification and drawings. Embodiments of the methods of invention explicitly include all combinations of dependent method claim steps, in any functional order. Embodiments of the methods of invention explicitly include, when referencing any device claim, a substation thereof to any and all other device claims, including all combinations of elements in device claims. Claims for devices and systems may be restricted to perform only the methods of embodiments or claims.

We claim:

1. A method of measuring efficacy of a first treatment of an autoimmune disease in a study animal in a vivarium comprising the steps of:
   (a) placing the study animal in a cage free of electronic penetrations in the vivarium and enrolling the study animal in a study;
   (b) electronically observing one or more animal activities in real-time of the study animal using a combination of electronic cameras, infrared (IR) lighting of the study animals, and electronic hardware including computation and communication hardware;
   (c) selecting a single "activity-drop metric" from the set: {regression analysis, LASSO, RANSAC, Monte Carlo} with an associated scalar "activity-drop value";
   (d) collecting a set of "nightly activity data" comprising values of the associated scalar activity drop value from electronically observing the study animal repeatedly and continually for a night;
   (e) identifying automatically three consecutive time regions in the nightly activity data: a "high-activity region," an "activity-drop region," and a "low-activity region;"
   (f) applying the activity-drop metric to the three consecutive regions, generating a nightly activity-drop value;
   (g) adding the nightly activity-drop value into an "animal health dataset," wherein the animal health dataset comprises the resulting nightly activity-drop values;
   (h) iterating steps (b) through (g) for sequential nights until a terminating condition is reached;
   wherein the study animal is housed in a home cage in the vivarium; and
   wherein the collected data comprises the animal health dataset.
   wherein the efficacy of the first treatment is a comparison of the animal health dataset to a reference treatment for the autoimmune disease;
   (i) removing the study animal from the study when the terminating condition is reached.

2. The method of claim 1 further comprising:
   (j) repeating steps (b) through (h) with multiple study animals in a first cohort;
   (k) computing an average of the nightly activity-drop values, from step (f), for each night, for each of the multiple animals in the first cohort; wherein the each night is time shifted for each of the multiple animals in the cohort to align to an each reference night of each animal;
   (l) adding the average of each night from step (k) into a cohort health dataset;
   wherein the efficacy of the first treatment further includes comparison of the cohort health dataset to the reference treatment for the autoimmune disease.

3. The method of claim 2 wherein:
   at least some of the multiple animals in the first cohort are housed in home cages in the vivarium wherein the home cages contain more than one animal; and
   wherein the collecting step (d) of the animals is performed on animals in their home cage.

* * * * *